US009132285B2

(12) United States Patent
Takayanagi et al.

(10) Patent No.: US 9,132,285 B2
(45) Date of Patent: Sep. 15, 2015

(54) RADIATION MEASURING DEVICE, PARTICLE BEAM THERAPY DEVICE PROVIDED WITH RADIATION MEASURING DEVICE, AND METHOD FOR CALCULATING DOSE PROFILE OF PARTICLE BEAM

(71) Applicant: HITACHI, LTD., Tokyo (JP)

(72) Inventors: Taisuke Takayanagi, Tokyo (JP); Shinichiro Fujitaka, Tokyo (JP); Chihiro Nakashima, Tokyo (JP); Koji Matsuda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/497,891

(22) Filed: Sep. 26, 2014

(65) Prior Publication Data

US 2015/0099918 A1    Apr. 9, 2015

(30) Foreign Application Priority Data

Oct. 4, 2013   (JP) .................................. 2013209133

(51) Int. Cl.
| A61N 5/00 | (2006.01) |
| A61N 5/10 | (2006.01) |
| G01T 1/29 | (2006.01) |
| G01T 1/02 | (2006.01) |

(52) U.S. Cl.
CPC ................ *A61N 5/1071* (2013.01); *G01T 1/02* (2013.01); *G01T 1/29* (2013.01)

(58) Field of Classification Search
CPC ........... A61N 5/1071; G01T 1/02; G01T 1/29
USPC ................................... 250/397, 492.1, 492.3
See application file for complete search history.

(56) References Cited

U.S. PATENT DOCUMENTS

2011/0231147 A1   9/2011  Takayanagi et al.
2013/0221213 A1*  8/2013  Takayanagi et al. ....... 250/252.1

FOREIGN PATENT DOCUMENTS

| JP | 2010-175309    | 8/2010 |
| JP | 2011-153833 A  | 8/2011 |
| JP | 2013-181756 A  | 9/2013 |

OTHER PUBLICATIONS

Shimbo et al., "Development of a Multi-layer Ion Chamber for Measurement of Depth Dose Distributions of Heavy-ion Therapeutic Beam for Individual Patients", Nippon ACTA Radiologica, 2000, vol. 60, pp. 274-279.

(Continued)

*Primary Examiner* — Michael Maskell
(74) *Attorney, Agent, or Firm* — Mattingly & Malur, PC

(57) ABSTRACT

A radiation measuring device having a plurality of sensors configured to generate charges in response to the radiation includes a signal processing device. The signal processing device uses an signal generated by a proton beam irradiation device upon changing of beam energy and causes accumulation values of charges output from the sensors to be separately stored in a main control device for each value of the energy. The main control device calculates depth dose profiles for values of the beam energy from the accumulation values stored in the main control device and representing the charges. The main control device calculates a range of the beam for each of the values of the beam energy from the depth dose profiles, corrects the depth dose profiles for the values of the beam energy using a correction coefficient that depends on the range and sums the corrected depth dose profiles.

10 Claims, 7 Drawing Sheets

(56) References Cited

OTHER PUBLICATIONS

Yajima et al., "Development of a multi-layer ionization chamber for heavy-ion radiotherapy", Physics in Medicine and Biology, 2009, vol. 54, pp. N107-N114.

Nichiporov et al., "Multichannel detectors for profile measurements in clinical proton fields", Medical Physics, Jul. 2007, vol. 34, No. 7, pp. 2683-2690.

Cirio et al., "Two-dimensional and quasi-three-dimensional dosimetry of hadron and photon beams with the Magic Cube and the Pixel Ionization Chamber", Physics in Medicine and Biology, 2004, vol. 49, pp. 3713-3724.

Brusasco et al., "A dosimetry system for fast measurement of 3D depth-dose profiles in charged-particle tumor therapy with scanning techniques", Nuclear Instruments and Methods in Physics Research B, 2000, vol. 168, pp. 578-592.

* cited by examiner

RADIATION MEASURING DEVICE, PARTICLE BEAM THERAPY DEVICE PROVIDED WITH RADIATION MEASURING DEVICE, AND METHOD FOR CALCULATING DOSE PROFILE OF PARTICLE BEAM

BACKGROUND OF THE INVENTION

The present invention relates to a radiation measuring device capable of detecting radiation such as a particle beam, a particle beam therapy device provided with the radiation measuring device, and a method for calculating a dose profile of a particle beam.

For particle beam therapy, a scanning irradiation method tends to be widely used.

In the scanning irradiation method, a target is divided into microscopic regions (hereinafter referred to as spots) that are each irradiated with a beam with a small radius (of $1\sigma=3$ to $20$ mm). After a predetermined dose has been applied to a certain spot, the beam irradiation is stopped and then, the next spot is scanned with the beam. Scanning electromagnets are used for scanning the beam in a direction perpendicular to its propagation direction (Hereinafter, the propagation direction is referred to as "a depth direction"; the direction perpendicular to the depth direction is referred to as "a lateral direction"). After a predetermined dose has been applied to each of all spots existing at a certain depth, the beam is next scanned in the depth direction. The beam scanning in the depth direction requires an energy change of the beam, the energy change being made by an accelerator or a range shifter. Thus, uniform doses are applied to all the spots or the overall target.

In this case, an operator uses a radiation measuring device to measure a position irradiated with the beam and a depth dose profile and analyzes results of the measurement so as to determine whether or not a particle beam therapy device is appropriately adjusted.

As a conventional radiation measuring device, a multilayer ionization chamber (MLIC) that has a structure of parallel plate ionization chambers stacked in a depth direction and is capable of measuring a depth dose profile of a particle beam at the same time is known (refer to JP-2011-153833-A and 'M. Shimbo, et al., "Development of a Multi-layer Ion Chamber for Measurement of Depth Dose Distributions of Heavy-ion Therapeutic Beam for Individual Patients", NIPPON ACTA RADIOLOGICA 2000 60 274-279').

SUMMARY OF THE INVENTION

The aforementioned multilayer ionization chamber can measure a depth dose profile of a particle beam at one time, which leads to an advantage of reducing the dose-measurement time, compared with a water phantom.

The water phantom is a radiation measuring device having a small sensor in a water tank. Due to the motor, the sensor can freely move in the water tank of the water phantom. When measuring a depth dose profile, however, the sensor needs to scan at each point of the dose profile, which requires a long time to confirm the performance of a therapy device.

However, since a multilayer ionization chamber described in JP-2011-153833-A is formed of a material different from water, there is a difference between a depth dose profile measured by the multilayer ionization chamber and a depth dose profile measured by the water phantom.

A device for particle beam therapy is adjusted using a dose profile of water as a standard. Thus, the multilayer ionization chamber is traditionally applicable to a part of confirmation items such as reproducibility of a depth dose profile and a range.

Thus, a radiation measuring device, which is typified by a multilayer ionization chamber and provided with a plurality of sensors, is requested to be applicable to a larger number of confirmation items for performance of a particle beam therapy device, and there is a demand to reduce a time for performance confirmation of therapy device.

It is an object of the present invention to provide a radiation measuring device having a reduced difference from water phantoms, a particle beam therapy device provided with the radiation measuring device, and a method for calculating a dose profile of a particle beam.

To achieve the above object, configurations described below can be employed. While the present invention contains a plurality of means for achieving the above object, the following configuration can be employed, for example: A radiation measuring device configured to detect a particle beam emitted by a particle beam therapy device includes a sensor unit having a plurality of sensor elements configured to generate charges in response to the particle beam; a signal processing device configured to separately collect, for each of the sensor elements, charges generated by each of the sensor elements of the sensor unit and perform an accumulation process; and a main control device configured to calculate a dose profile from accumulation values calculated in the accumulation process performed by the signal processing device. The signal process device includes an accumulating unit configured to separately accumulate, for each of the sensor elements, charges output from each of the sensor elements for each timing of the signal reception from the particle beam irradiation device, and an output unit configured to output the accumulation values calculated in the accumulation process performed by the accumulating unit to the main control device. The main control device includes a storage unit configured to store the accumulation values calculated for each times of the signal reception from the signal processing device, a first calculator configured to calculate, from the accumulation values stored in the storage unit, the dose profile for each timing of the signal reception, and a second calculator configured to correct the dose profile for each timing of the signal reception calculated by the first calculator, and sum the corrected dose profiles.

According to the invention, a radiation measuring device, which is provided with a plurality of sensors and typified by a multilayer ionization chamber, is capable of measuring a dose with high precision and has a reduced difference from water phantoms. Thus, the multilayer ionization chamber is applicable to a larger number of confirmation items, and a time for performance confirmation of a therapy device is reduced.

DESCRIPTION OF THE PREFERRED EMBODIMENTS

Figure 1:
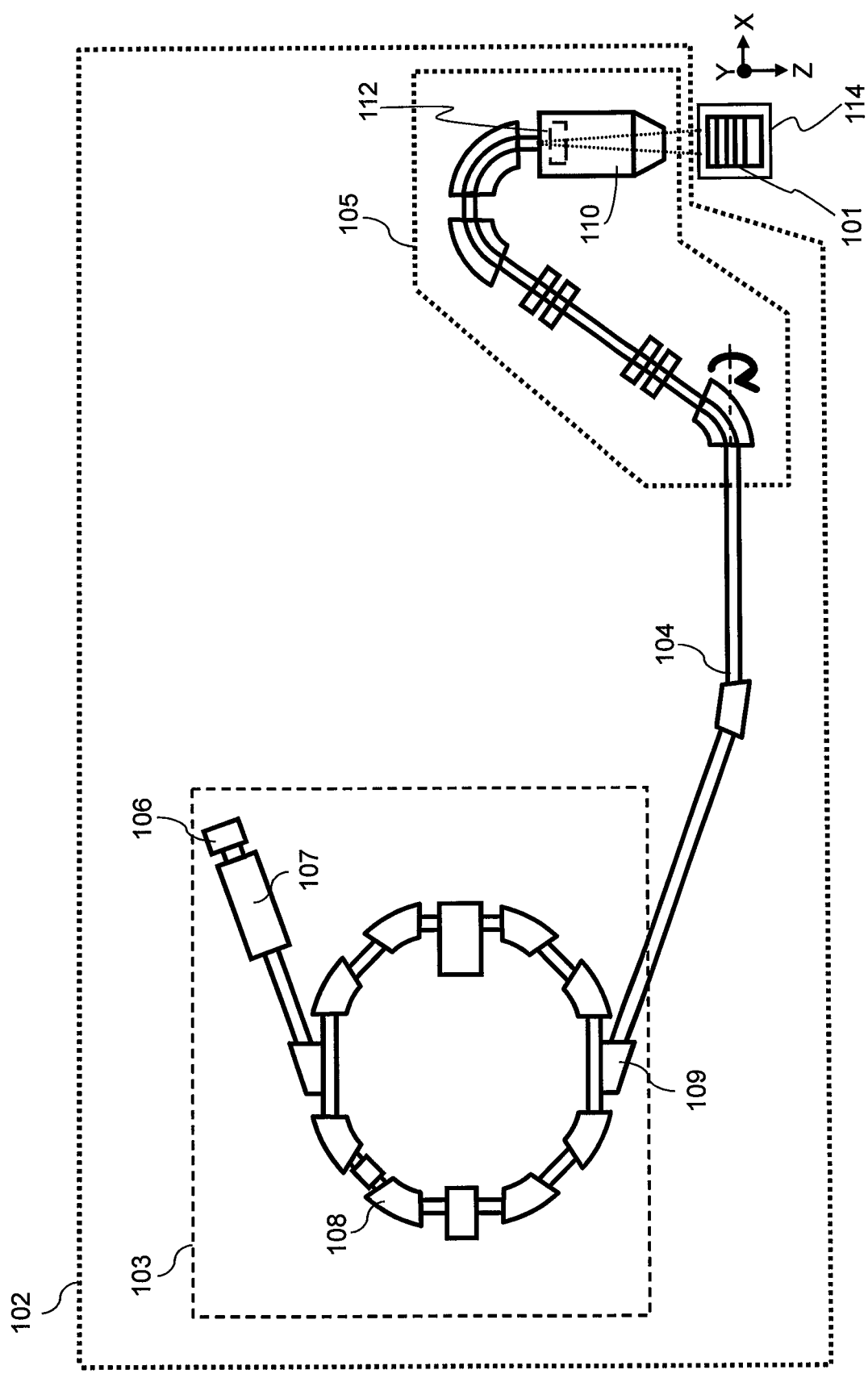
FIG. 1 is a diagram illustrating an overall configuration of a particle beam therapy device according to an embodiment of the invention.

Hereinafter, an embodiment of a radiation measuring device according to the invention, a particle beam therapy device provided with the radiation measuring device, and a method for calculating a dose profile of a particle beam is described with reference to the accompanying drawings.

In a particle beam irradiation device that uses a scanning irradiation method, scanning electromagnets and the like are adjusted so that a beam is scanned on a designated position in a lateral direction, and an accelerator and the like are adjusted so that the beam has a designated range. The range indicates a depth that the beam reaches, the range depending on initial energy of the beam.

In general, in order to confirm results of the adjustment of the particle beam irradiation device, the radiation measuring device measures a position irradiated with the beam, a depth dose profile, and the like. A depth dose profile of a particle beam having a single energy value is referred to as a Bragg curve. The range is calculated from the Bragg curve. In volume irradiation, a dose profile in a lateral direction is also measured. The volume irradiation is to form a uniform dose profile in an arbitrary region (referred to as an affected area or a target) of an object to be irradiated, in accordance with a procedure of the scanning irradiation method.

The radiation measuring device is composed of a signal processing device and a sensor configured to output an electric signal mainly in response to radiation. A representative example of the sensor is an ionization chamber.

The ionization chamber has a structure in which an ionization layer (formed of a material such as air or rare gas) is sandwiched between two electrodes. A high voltage is applied to one of the electrodes so that an electric field is formed over the ionization layer. Ionization charges generated from the ionization layer upon irradiation with the beam are collected. The amount of the ionization charges is proportional to the amount [MeV] of energy loss of the beam in the ionization layer. In addition, the amount of the energy loss is proportional to a dose at a position at which the ionization chamber is installed. The signal processing device converts the charges generated from the ionization layer into a digital value and displays the digital value on a display or the like. The digital value is further stored in a storage device such as a hard disk drive.

A radiation measuring device that has a structure of a plurality of parallel plate ionization chambers stacked in a depth direction is referred to as a multiplayer ionization chamber (hereinafter, referred to as "MLIC"). The parallel plate ionization chambers each have a structure in which an ionization layer is sandwiched between two plate-like electrodes in parallel. A dose D (unit [Gy]) is calculated by multiplying the amount of charges (unit [C]) obtained from the ionization layer by a conversion factor (unit [Gy/C]).

MLIC can measure a depth dose profile of a particle beam at one time, which leads to an advantage of reducing the dose-measurement time, compared with a water phantom.

As described above, the water phantom, which is a radiation measuring device having a small sensor in a water tank, has a disadvantage of taking a long time in measuring a dose.

The multiplayer ionization chamber is formed of a material such as glass epoxy different from water. Thus, the multiplayer ionization chamber and the water phantom are different from each other with regard to a nuclear cross section of a particle beam and a region of range straggling in the multilayer ionization chamber. Furthermore, there is a difference between a depth dose profile measured by the multiplayer ionization chamber and a depth dose profile measured by the water phantom.

A radiation measuring device, which has a reduced difference from the water phantoms and is provided with a plurality of sensors typified by a multilayer ionization chamber, and a particle beam therapy device having the radiation measuring device, are provided according to the invention and described below.

Configurations and operations of a radiation measuring device and a particle beam therapy device according to the embodiment of the invention are described below with reference to FIGS. 1 to 6.

FIG. 1 is a diagram illustrating an overall configuration of the particle beam therapy device provided with the radiation measuring device according to the embodiment of the invention.

The particle beam therapy device includes the radiation measuring device 101 and a proton beam irradiation device 102.

The radiation measuring device 101 adjusts the proton beam irradiation device 102 that uses the scanning irradiation method. The radiation measuring device 101 evaluates performance of the proton beam irradiation device 102 by measuring a depth dose profile of a beam emitted by the proton beam irradiation device 102. Detailed configurations and the like of the radiation measuring device 101 are described later.

Although the proton beam irradiation device 102 is described as a particle beam irradiation device as an example, the radiation measuring device according to the invention is also applicable to a heavy particle beam irradiation device that uses particles (a carbon beam or the like) having a greater mass than protons. In addition, the proton beam irradiation device 102 is not limited to the device that uses the scanning irradiation method; the proton beam irradiation device 102 may alternatively emit protons using a scatterer irradiation method.

As illustrated in FIG. 1, the proton beam irradiation device 102 includes a proton generating device 103, a proton transporting device 104, and a rotary irradiation device 105. Although the embodiment describes the rotary irradiation device 105 that has a rotary gantry as an example, the irradiation device may be of a fixed type.

The proton generating device 103 includes an ion source 106, an upstream-side accelerator 107 (for example, a linear accelerator), and a synchrotron 108. Proton ions generated by the ion source 106 are first accelerated by the upstream-side accelerator 107. A proton beam (hereinafter merely referred to as a beam) output from the upstream-side accelerator 107 is accelerated by the synchrotron 108 so as to have predetermined energy. After that, the beam is output to the proton transporting device 104 from an output deflector 109. Finally, the beam passes through the rotary irradiation device 105 to irradiate the radiation measuring device 101.

The rotary irradiation device 105 includes the rotary gantry (not illustrated) and an irradiation nozzle 110. The irradiation nozzle 110, installed at the rotary gantry, rotates with the rotary gantry. A part of the proton transporting device 104 is attached to the rotary gantry. In the embodiment, the synchrotron 108 is used as a device for accelerating the proton beam, but may be replaced with a cyclotron or a linear accelerator.

Next, an outline of the scanning irradiation method achieved by the irradiation nozzle 110 according to the embodiment is described.

According to the scanning irradiation method, an irradiation range is divided into microscopic regions (spots), and the each spots are irradiated with the beam. After a predetermined dose has been applied to a spot, the irradiation is stopped and then, the beam is scanned on a next predetermined spot. When scan the beam in the lateral direction, two pairs of scanning electromagnets (not illustrated) included in the irradiation nozzle 110 are used.

After a predetermined dose has been applied to each of all spots located at a certain depth, the irradiation nozzle 110 begins to scan the beam in the depth direction. The beam energy is changed by changing a condition of the synchrotron 108 or using a range shifter (not illustrated) installed in the irradiation nozzle 110 or the like. Thus, the beam is scanned in a depth direction.

By repeating such a procedure, uniform dose profiles are formed as a result.

The irradiation nozzle 110 has a dose monitor 112 for detecting a dose of the output beam (irradiation beam). Although the irradiation is stopped when the predetermined dose has been applied to a spot, the beam may be not stopped and directed at the next spot, which is called the "raster scanning method."

In the embodiment, a straight line through which the center of the beam passes in a state in which the scanning electromagnets are not excited is defined as a beam axis. In addition, a point at which a rotational axis of the rotary irradiation device 105 intersects with the beam axis is defined as an isocenter. In the scanning irradiation method, the spread of the beam in the lateral direction in the vicinity of the isocenter is $1\sigma=3$ mm to 20 mm.

The radiation measuring device 101 is installed on a patient couch 114. The patient couch 114 can move the radiation measuring device 101 in a direction of the beam axis (Z-axis direction). In addition, the patient couch 114 can move the radiation measuring device 101 in two directions perpendicular to the Z-axis direction (X-axis direction and Y-axis direction).

Figure 2:
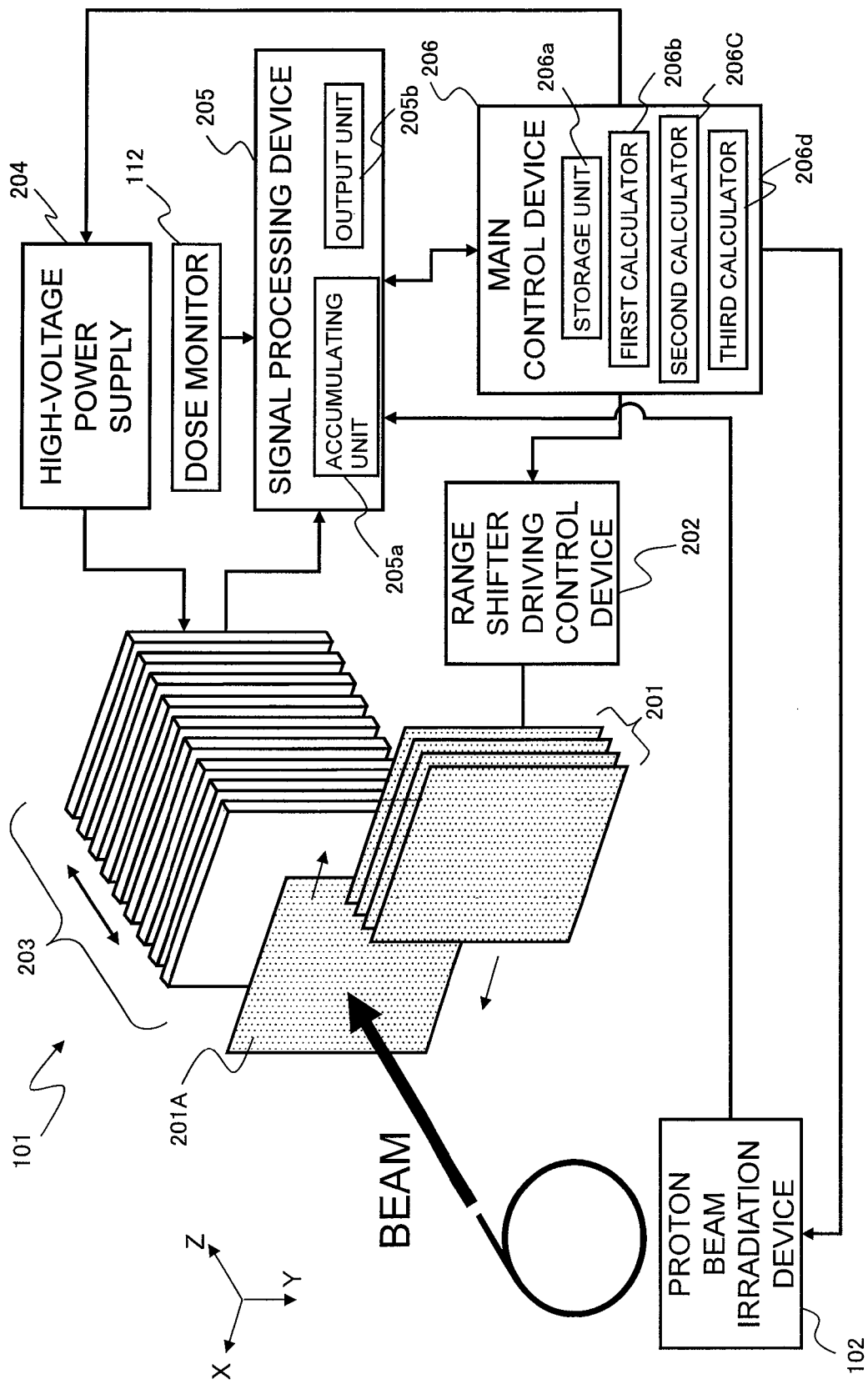
FIG. 2 is a block diagram illustrating a configuration of a radiation measuring device according to the embodiment of the invention.

Next, a detailed configuration of the radiation measuring device 101 according to the embodiment is described with reference to FIG. 2. FIG. 2 is a block diagram illustrating the detailed configuration of the radiation measuring device according to the embodiment of the invention. In FIG. 2, reference numerals and symbols that are the same as those illustrated in FIG. 1 represent the same parts as illustrated in FIG. 1.

The radiation measuring device 101 includes range shifters 201, a range shifter driving control device 202, a sensor unit 203, a high-voltage power supply 204, a signal processing device 205, and a main control device 206.

The range shifters 201 are located at the upstream side of the sensor unit 203 in the direction in which the beam propagates (hereinafter referred to as a depth direction or a Z-axis direction). The range shifters 201 include a plurality of energy absorbers 201A having different water equivalent thicknesses. In the embodiment, the range shifters 201 include five energy absorbers 201A having water equivalent thicknesses of 0.2 mm, 0.4 mm, 0.8 mm, 1.6 mm, and 3.2 mm. When the range shifter driving control device 202 transmits a signal to the range shifters 201, the range shifters 201 operate a motor (not illustrated) and insert and retract the energy absorbers 201A into and from positions through which the beam passes. When the beam passes through the energy absorbers 201A, a measurement position of, the radiation measuring device 101 changes by a distance corresponding to the water equivalent thicknesses in the depth direction. In this manner, the radiation measuring device 101 according to the embodiment adjusts its measurement position in the depth direction.

The measurement position can be adjusted within a range that is equal to the water equivalent thickness obtained by combining the five energy absorbers 201A; the range is from 0.2 mm to 6.2 mm, at intervals of 0.2 mm.

A material of the energy absorbers 201A, the number of the energy absorbers 201A, and the water equivalent thicknesses of the energy absorbers 201A are arbitrary. In the embodiment, plates formed of acrylonitrile butadiene styrene (ABS) resin are used as the energy absorbers 201A. A water equivalent thickness of an object indicates the thickness of water required to give, to a particle beam, the amount of energy loss equal to the particle beam that has passed through the object.

Figure 3:
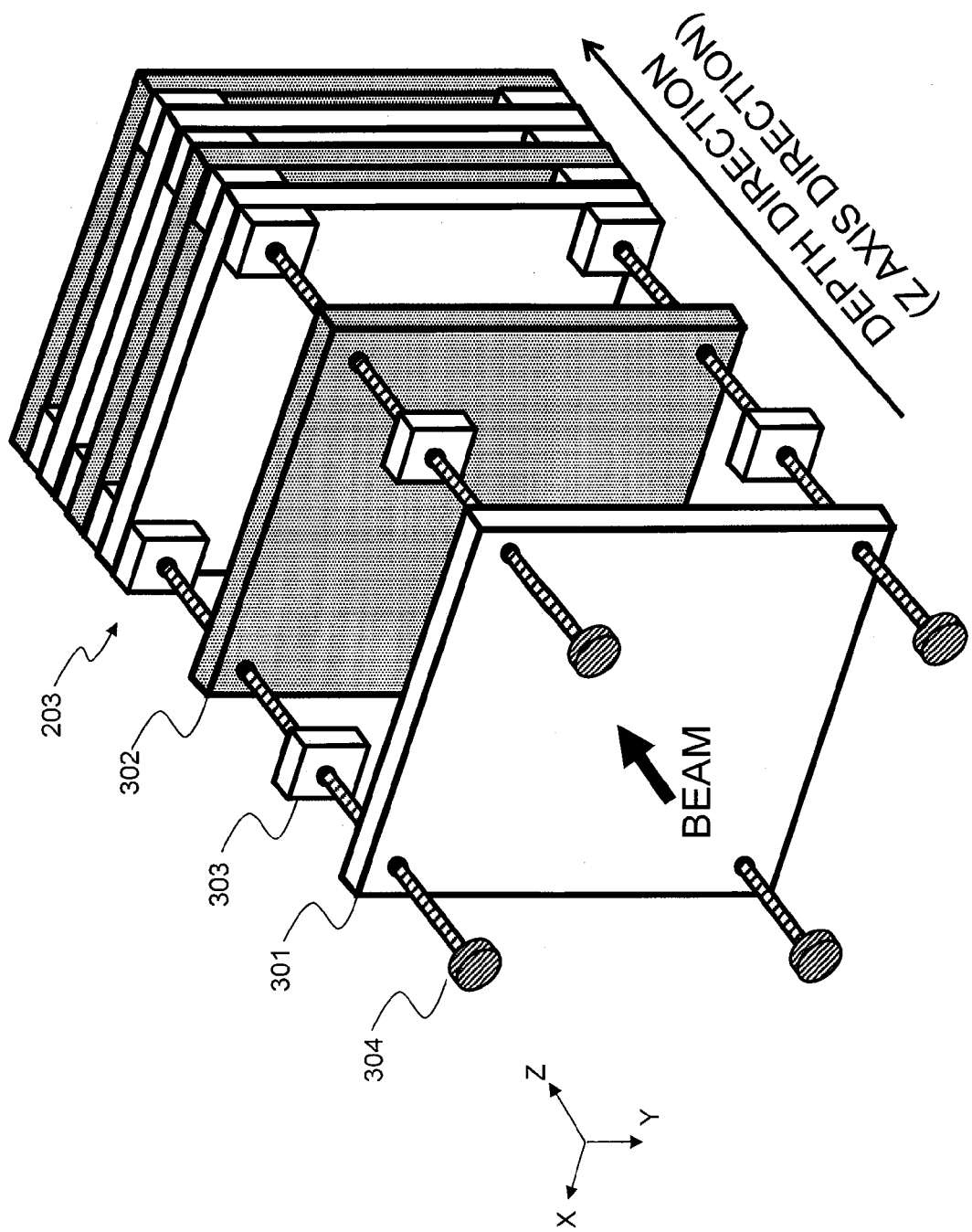
FIG. 3 is a perspective view of a configuration of a sensor unit used for the radiation measuring device according to the embodiment of the invention.

Next, a configuration of the sensor unit 203 used for the radiation measuring device 101 according to the embodiment is described. FIG. 3 is a perspective view of the configuration of the sensor unit used for the radiation measuring device of the particle beam therapy device according to the embodiment of the invention. In FIG. 3, reference symbols that are the same as those illustrated in FIG. 2 indicate the same parts as illustrated in FIG. 2.

As illustrated in FIG. 3, the sensor unit 203 has a structure in which charge collection printed boards 301 and high-voltage application printed boards 302 are alternately stacked in the depth direction (Z-axis direction). The number of the stacked charge collection printed boards 301 and the number of the stacked high-voltage application printed boards 302 are arbitrary, but need to be 1 or more. Although three charge collection printed boards 301 and three high-voltage application printed boards 302 are stacked in an example illustrated in FIG. 3, 50 charge collection printed boards 301 and 50 high-voltage application printed boards 302 are actually stacked, for example.

Spacers 303 are arranged between the charge collection printed boards 301 and the high-voltage application printed boards 302. Ionization layers are formed between the charge collection printed boards 301 and the high-voltage application printed boards 302 by the insertion of the spacers 303. The spacers 303 are insulating bodies.

In the embodiment, if 51 charge collection printed boards 301 and 51 high-voltage application printed boards 302 are stacked, the number of ionization layers is 100. The ionization layers are filled with ionized gas. In the embodiment, the ionization layers are open to air, and the air is used as the ionized gas. The ionization layers may be sealed and have a configuration in which ionized gas such as argon is circulated by a gas cylinder or the like. In addition, the stacked charge collection printed boards 301, the stacked high-voltage application printed boards 302, and the spacers 303 are fixed using bolts 304. The fixing method is not limited to this as long as the charge collection printed boards 301, the high-voltage application printed boards 302, and the spacers 303 are stacked and fixed in a stable manner.

The charge collection printed boards 301 and the high-voltage application printed boards 302 are glass epoxy plates that each have front and back surfaces (X-Y surfaces) on which electrodes are deposited and that are perpendicular to the depth direction. The electrodes are formed of copper and plated with nickel and gold. The printed boards, however, are not limited to the glass epoxy plates as long as the printed boards are insulating bodies. The electrodes are not limited to copper, nickel, and gold as long as the electrodes are conductive bodies. In the embodiment, the charge collection printed boards 301 and the high-voltage application printed boards 302 have thicknesses nearly equal to each other, and both have a water equivalent thickness of 4.0 mm.

Figure 4:
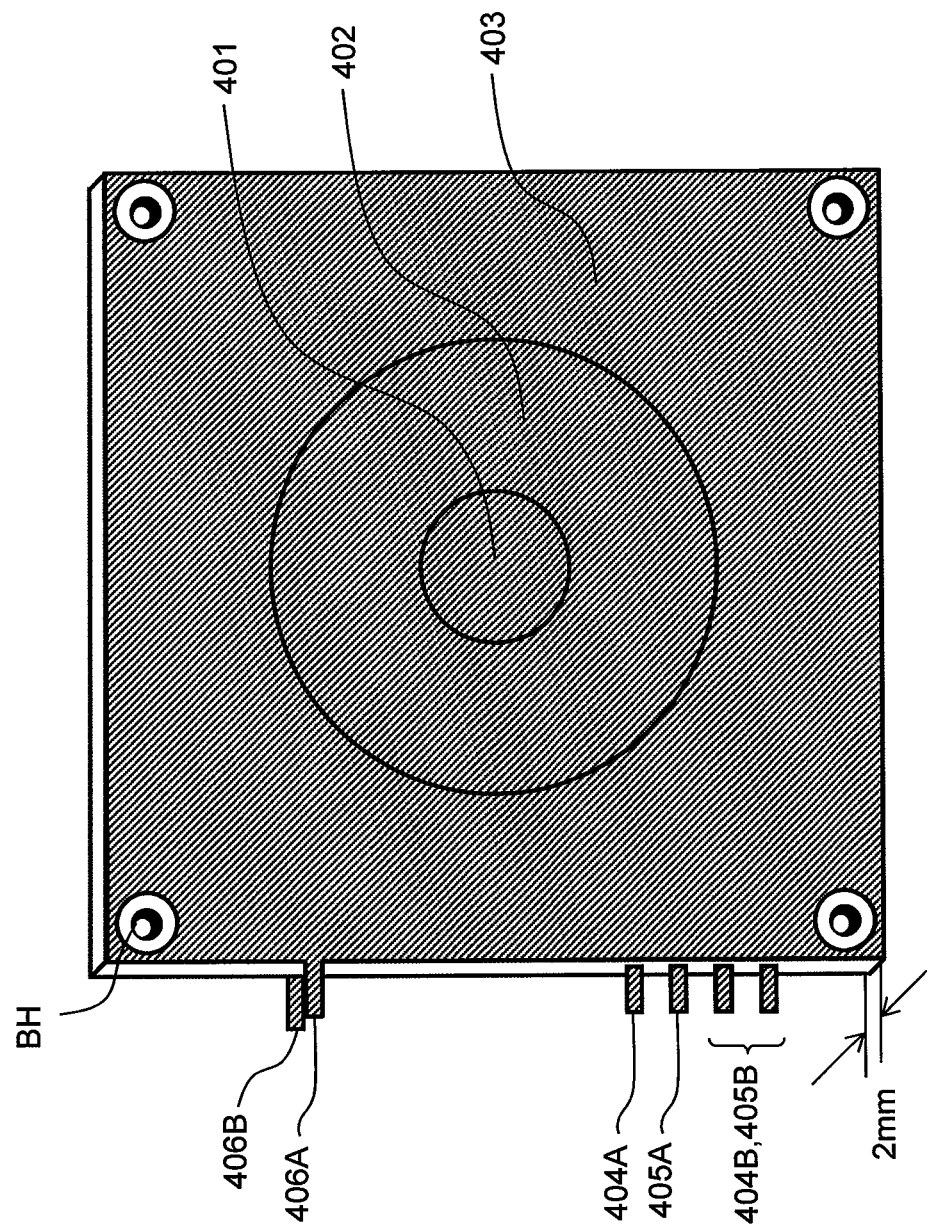
FIG. 4 is a perspective view of a configuration of a charge collection printed board used for the sensor unit of the radiation measuring device according to the embodiment of the invention.

Next, configurations of the charge collection printed boards 301 used for the sensor unit 203 of the radiation measuring device 101 according to the embodiment are described with reference to FIG. 4. FIG. 4 is a perspective view of the configuration of each of the charge collection printed boards 301 used for the sensor unit 203 of the radiation measuring device 101 according to the embodiment of the invention.

As illustrated in FIG. 4, the electrodes of both front and back surfaces of each of the charge collection printed board 301 are each electrically divided into three regions. On each of the front and back surfaces of each of the charge collection printed boards 301, a region that includes the center of the charge collection printed board 301 (central region) is treated as a small electrode (first electrode) 401, a region that surrounds the small electrode 401 is treated as a large electrode (second electrode) 402, and a region that is located at the outermost side is treated as a guard electrode (third electrode) 403.

The small electrode 401 is connected to a conducting wire 404A, the large electrode 402 is connected to a conducting wire 405A, and the guard electrode 403 is connected to a conducting wire 406A. An end of the conducting wire 404A connected to the small electrode 401 and an end of the conducting wire 405A connected to the large electrode 402 are connected to an input of the signal processing device 205 through an internal layer of the printed board. Specifically, the conducting wire 404A connects the small electrode 401 to the signal processing device 205, and the conducting wire 405A connects the large electrode 402 to the signal processing device 205. An end of the conducting wire 406A connected to the guard electrode 403 is grounded.

The guard electrode 403 prevents a leak current from flowing from the high-voltage application printed boards 302 to the small electrode 401 and the large electrode 402.

An electrode composed of the small electrode 401 and the large electrode 402 is formed in a shape that is sufficiently larger than the beam (1σ=3 to 20 mm at the isocenter) spreading like a two-dimensional Guassian distribution in the lateral direction due to scattering and drift of the beam within the radiation measuring device 101. The electrodes of the charge collection printed board 301 have a symmetric structure on both surfaces and collect charges from the ionization layers facing the front and back surfaces.

A conducting wire 406B is connected to the guard electrode located on the back surface and is grounded. A conducting wire 404B is connected to the small electrode located on the back surface and is connected to the signal processing device 205, while a conducting wire 405B is connected to the large electrode located on the back surface and is connected to the signal processing device 205.

The charge collection printed board 301 has bolt holes BH at four corners of the charge collection printed board 301. The bolts 304 illustrated in FIG. 3 extend through the bolt holes BH.

Figure 5:
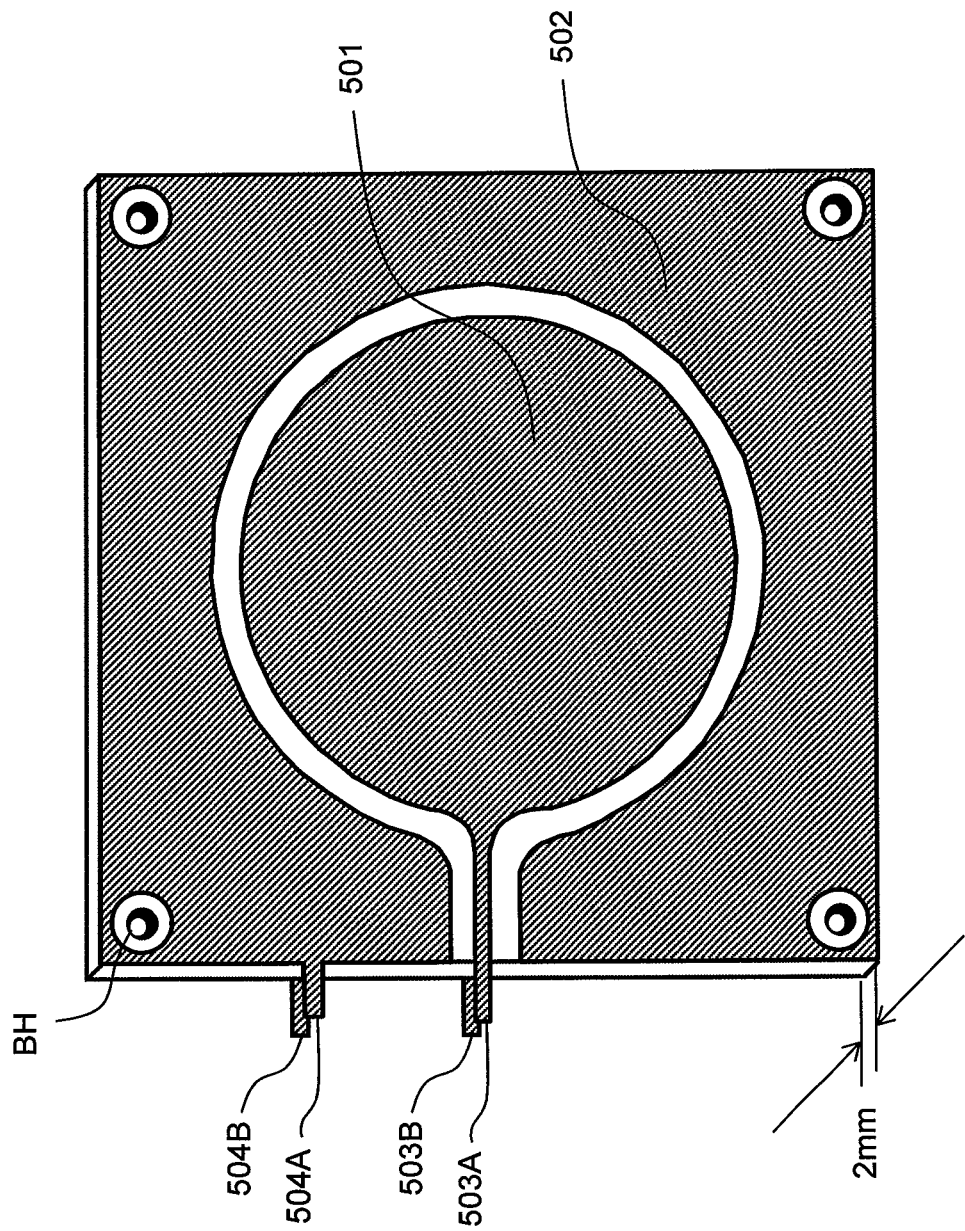
FIG. 5 is a perspective view of a configuration of a high-voltage application printed board used for the sensor unit of the radiation measuring device according to the embodiment of the invention.

Next, configurations of the high-voltage application printed boards 302 used for the sensor unit 203 of the radiation measuring device 101 according to the embodiment are described with reference to FIG. 5. FIG. 5 is a perspective view of the configuration of each of the high-voltage application printed boards 302 used for the sensor unit 203 of the radiation measuring device 101 according to the embodiment of the invention.

As illustrated in FIG. 5, the electrodes of both front and back surfaces of each of the high-voltage application printed boards 302 are each electrically divided into two regions, a central region and an outer region. The central region is treated as a high-voltage application electrode 501, and the outer region is treated as a guard electrode 502.

The high-voltage application electrode 501 is connected to a conducting wire 503A, and the guard electrode 502 is connected to a conducting wire 504A. The conducting wire 503A connects the high-voltage application electrode 501 to the high-voltage power supply 204 and applies a high voltage (of several thousand volts or lower in absolute value) supplied from the high-voltage power supply 204 to the high-voltage application electrode 501. An end of the conducting wire 504A connected to the guard electrode 502 is grounded.

The guard electrode 502 prevents a leak current from flowing from the high-voltage application printed board 302 to the small and large electrodes 401 and 402 on the charge collection printed boards 301.

Since the small and large electrodes 401 and 402 of the charge collection printed boards 301 are at approximately 0 volts, electric fields are formed in the depth direction at the ionization layers.

Since the electrodes of the high-voltage application printed board 302 have a symmetric structure on both surfaces, the high-voltage is applied to the high-voltage application electrodes located on the front and back surfaces of the high-voltage application printed board 302.

A conducting wire 504B is connected to the guard electrode located on the back surface and is grounded. In addition, a conducting wire 503B is connected to the high-voltage application electrode located on the back surface and is connected to the high-voltage power supply 204.

In addition, the high-voltage application printed board 302 has bolt holes BH at four corner of the high-voltage application printed board 302. The bolts 304 illustrated in FIG. 3 extend through the bolt holes BH of the high-voltage application printed board 302.

Since the sensor unit 203 has the above structure, the distance between the center of the charge collection printed board 301 and that of the adjacent charge collection printed board 302 is associated with one sensor in the depth direction. The average of the water equivalent thicknesses of the sensors is 4.0 mm. Thus, if the range shifters 201 are not used, the radiation measuring device 101 according to the embodiment can measure a Bragg curve at intervals of 4.0 mm.

In the embodiment, the actual thicknesses of the charge collection printed boards 301 and high-voltage application printed boards 302 are approximately 2 mm. In addition, the thicknesses of the spaces or the thicknesses of the ionization layers located between the charge collection printed boards 301 and the high-voltage application printed boards 302 are 2 mm. Thus, the actual thicknesses of the sensors are equal to the water equivalent thicknesses (having average of 4.0 mm).

If the radiation measuring device 101 is designed so that the water equivalent thicknesses are equal to the actual thicknesses of printed boards 301 and 302, it is not necessary to perform an inverse square correction of measured values. The beam in particle beam therapy can be approximately regarded as being uniformly irradiated with the beam from a point source. Thus, the number of beam particles per unit of area (fluence) decreases in inverse proportion to the square of a distance from the point source. Thus, if an actual distance between a certain sensor and a front surface of the sensor unit 203 is different from a distance calculated in water equivalent thickness, a correction (inverse square correction) of a difference between the numbers of particles needs to be performed. Since the inverse square correction can be performed in the invention, it is not necessarily necessary to match the thicknesses of the sensors with the water equivalent thicknesses.

Referring to FIG. 2, the signal processing device 205 includes an accumulating unit 205a and an output unit 205b.

The accumulating unit 205a separately accumulates ionized charges collected by the small and large electrodes of each of layers of the sensor unit 203 every time the accumulating unit 205a receives a signal from the proton beam irradiation device 102.

The proton beam irradiation device 102 has a dose monitor 112 located in a path of the beam in the irradiation nozzle 110 for monitoring a dose of the beam for each spot. The dose monitor 112 is a parallel plate ionization chamber and outputs, to the signal processing unit 205, ionized charges generated by the dose monitor 112 and proportional to the amount of energy loss of the beam in the ionization layers. The accumulating unit 205a of the signal processing device 205 accumulates the ionized charges output from the dose monitor (not shown).

In addition, the signal processing device 205 uses the accumulating unit 205a to digitalize results of the accumulation of the ionized charges collected by the small and large electrodes of the layers of the sensor unit 203 and results of the accumulation of the ionized charges collected from the dose monitor 112. Then the signal processing device 205 outputs the digitalized results to the main control device 206 through the output unit 205b.

The main control device 206 uses accumulation values obtained from the dose monitor 112 to normalize accumulation values obtained from the sensor unit 203 and thereby calculates dose profiles and corrects a dispersion of measurement results, the dispersion being caused by a variation of the irradiation-beam amount.

The main control device 206 includes a storage unit 206a, a first calculator 206b, a second calculator 206c, and a third calculator 206d.

The storage unit 206a stores accumulation values input from the signal processing device 205 each time the main control device 206 receives a signal from the proton beam irradiation device 102.

The first calculator 206b calculates each time's dose profiles from accumulation values obtained from the sensor unit 203 which are stored in the storage unit 206a and accumulation values obtained from the dose monitor 112.

The second calculator 206c corrects the dose profiles calculated by the first calculator 206a at the times of the reception and sums the dose profiles, the second calculator 206c using a correction coefficient C (E, x) that depends on the energy of the particle beam.

The third calculator 206d calculates a range of the particle beam from the each time's dose profiles calculated by the first calculator 206a.

Since the electrodes of the charge collection printed boards 301 are each formed in a double concentric circular shape, the radiation measuring device 101 according to the embodiment of the invention can measure two types of dose profiles: a percentage depth dose (PDD) and an integral depth dose (IDD).

The PDD indicates a dose profile of radiation on a certain axis in the depth direction (beam axis in general). The IDD is obtained by integrating doses in the lateral direction and indicates a dose profile for each depth.

The radiation measuring device 101 according to the embodiment can measure the PDD by using only signals from the small electrodes 401. The radiation measuring device 101 according to the embodiment can measure the IDD by adding the signals obtained from the small electrodes 401 to signals obtained from the large electrodes 402.

However, the shapes of the electrodes of the charge collection printed boards 301 according to the embodiment of the invention are arbitrary. For example, the electrodes of the charge collection printed boards 301 may be divided into parts arranged in a matrix form or into stripe parts in order to measure dose profiles in the lateral direction, and ionized charges may be obtained from the divided electrodes. In addition, the shapes of the electrodes of the high-voltage application printed boards 302 may be arbitrary as long as a desired distribution of electric fields can be formed within the ionization layers.

In the embodiment, the radiation sensors that are composed of the ionization layers and the pairs of the electrodes sandwiching the ionization layers are referred to as ionization chambers. It can be said that the sensor unit 203 according to the embodiment has a structure in which the ionization chambers are stacked in the depth direction.

According to the invention, the ionization chambers may be replaced with semiconductor detectors or scintillation counters. Specifically, even if the sensor unit 203 has a structure in which the semiconductor detectors or the scintillation counters are stacked in the depth direction, the same effects as the embodiment can be obtained. In this case, the semiconductor detectors or the scintillation counters react to energy loss of radiation in the semiconductor detectors or the scintillation counters and output electric signals in response to the energy loss.

In general, the semiconductor detectors are semiconductor elements formed by bonding p-type semiconductors and n-type semiconductors. When the semiconductor detectors are used as the radiation sensors, inverse voltages are applied to elements of the semiconductor detectors to expand depletion layers of bonded parts of the semiconductor detectors. The depletion layers serve as the ionization layers. When radiation is incident on the depletion layers, pairs of holes and electrons, of which the number is proportional to the amount of energy loss of the radiation, are generated. The pairs of holes and electrons are drifted in accordance with the orientations of electric fields within the depletion layers and output as charges to the signal processing devices 205 from electrodes connected to the p-type and n-type semiconductors.

The scintillation counters are radiation sensors composed of a fluorescent material (NaI crystal, GSO crystal, organic EL, or the like) and optical detectors (optical photomultipliers). The fluorescent material serves as the ionization layers. When radiation is incident on the scintillation counters, the fluorescent material emits fluorescence with an amount proportional to energy loss of the radiation. The optical detectors generate charges with an amount proportional to the amount of the emitted fluorescence and output the charges to the signal processing device 205.

Next, a procedure for measuring an IDD of the proton beam using the radiation measuring device 101 according to the embodiment is described.

First, the radiation measuring device 101 is fixed onto the patient couch 114 in an irradiation chamber of the proton beam irradiation device 102.

Next, the patient couch 114 is moved so that the position of the radiation measuring device 101 is determined using, as a standard, a laser marker for determination of the position of a patient. In the embodiment, the position of the radiation measuring device 101 is determined so that the beam axis passes through the centers of the small electrodes 401 of the layers of the sensor unit 203.

After of the position has been determined, an operator turns on a power supply of the range shifter driving control device 202, the high-voltage power supply 204, and the signal processing device 205, by use of the main control device 206. All the energy absorbers 201A of the range shifters 201 stand by while being placed out of the path of the beam.

Next, the operator sets desired measurement intervals in the main control device 206. In the embodiment, the operator sets the measurement intervals to a relatively large value of 1.0 mm on the assumption that the IDD measurement is performed in a case where incidence the beam energy is high or where a wide Bragg peak is obtained. In addition, the operator sets, using the main control device 206, irradiation conditions (the beam energy, the positions of spots to be irradiated, the number of the spots to be irradiated, and the like) of the proton beam irradiation device 102, thereby instructing to start the irradiation with the beam.

The signal processing device 205 starts accumulating charges, and the radiation measuring device 101 is irradiated with the beam in accordance with the conditions set in the main control device 206 by the operator. In the IDD measurement according to the embodiment, each spot that is located on the beam axis is irradiated with the beam, and thus the scanning electromagnets included in the irradiation nozzle 110 are not excited.

After the irradiation with the beam has been completed, the proton beam irradiation device 102 transmits an irradiation completion signal to the signal processing device 205. Upon receiving the irradiation completion signal, the signal processing device 205 stops accumulating of charges and digitalizes accumulation values representing charges obtained from the small and large electrodes 401 and 402 of the layers of the sensor unit 203, thereby transmitting the accumulation values to the main control device 206. The signal processing device 205 also digitalizes accumulation values representing ionized charges obtained from the dose monitor 112 and transmits the accumulation values to the main control device 206.

The main control device 206 stores the transmitted accumulation values. In addition, the main control device 206 normalizes the accumulation values obtained from the sensor unit 203 using the accumulation values obtained from the dose monitor 112, then the main control device 206 stores the normalized accumulation values. After the completion of the storage, the signal processing device 205 resets all accumulation values stored therein.

Next, the main control device 206 instructs the range shifter driving control device 202 to insert the energy absorbers 201A. In the embodiment, the range shifter driving control device 202 inserts the energy absorbers 201A having the water equivalent thicknesses of 0.2 mm and 0.8 mm.

When the insertion of the energy absorbers 201A is completed, the main control device 206 reinstructs the proton beam irradiation device 102 to perform the irradiation with the beam in accordance with the conditions initially set by the operator.

The signal processing device 205 starts accumulating charges, and the radiation measuring device 101 is irradiated with the beam.

When the irradiation with the beam is completed and the signal processing device 205 receives the irradiation completion signal, the signal processing device 205 stops accumulating charges. The signal processing device 205 then digitalizes accumulation values representing ionized charges, with the accumulation values being obtained from the small and large electrodes 401 and 402 of the layers of the sensor unit 203. Then, the signal processing device 205 transmits the accumulation values to the main control device 206. In addition, the signal processing device 205 digitalizes accumulation values representing ionized charges, with the accumulation values being obtained from the dose monitor 112. The signal processing device 205 then transmits the accumulation values to the main control device 206.

The main control device 206 stores the transmitted accumulation values. In addition, the main control device 206 uses the accumulation values obtained from the dose monitor 112 to normalize the accumulation values obtained from the sensor unit 203 and also stores the accumulation values. After the completion of the storage, the signal processing device 205 resets all accumulation values stored therein.

In addition, the main control device 206 instructs the range shifter driving control device 202 to insert the energy absorbers 201A having the water equivalent thicknesses of 0.4 mm and 1.6 mm. The energy absorbers 201A having the water equivalent thicknesses of 0.2 mm and 0.8 mm are retracted from the beam path.

When the insertion and retraction of the energy absorbers 201A are completed, the main control device 206 reinstructs the proton beam irradiation device 102 to perform the irradiation with the beam in accordance with the conditions initially set by the operator. In order to measure Bragg curves at the measurement intervals of 1.0 mm, the measurement is repeated while the total water equivalent thicknesses of the energy absorbers 201A inserted onto the beam axis are 0.0 mm (all the energy absorbers 201A are placed out of the path of the beam), 1.0 mm, 2.0 mm, and 3.0 mm.

When the range shifters are operated in the aforementioned manner, the operator can measure IDDs at the intervals of 1.0 mm using the radiation measuring device 101 having the sensors arranged at the intervals of 4 mm according to the embodiment.

When the driving of all the range shifters is terminated, measurement results are processed.

First, when the total water equivalent thickness of the energy absorbers 201A inserted is r, accumulated charge obtained from small electrodes 401 facing an ionization layer i is represented by Qs(i, r) and accumulated charge obtained from large electrodes 402 facing the ionization layer i is represented by Ql(i, r). As described above, these values are normalized by the main control device 206 using accumulation values obtained from the dose monitor 112. When all measurements are completed, the main control device 206 causes the first calculator 206b to sum Qs(i, r) and Ql(i, r) and calculate an IDD(i, r). Specifically, the first calculator 206b calculates the following Equation (1).

$$IDD(i,r)=N\times(Qs(i,r)+Ql(i,r)) \quad (1)$$

where, N is a conversion factor for converting charges into a dose. The conversion factor is stored in the main control device 206 by the operator in advance. The charge collection printed boards 301, the high-voltage application printed boards 302, and the water equivalent thicknesses of the ionization layers are measured by the operator in advance, and information of the charge collection printed boards 301, the high-voltage application printed boards 302, and the water equivalent thicknesses of the ionization layers is registered in the main control device 206. The main control device 206 causes the first calculator 206b to convert the IDD(i, r) into an IDD(x) on the basis of the registered information. In this case, x is a depth from a water surface.

In order to reduce a difference between the measured value and a value measured by a water phantom, the main control device 206 causes the second calculator 206c to correct the IDD(x) using a correction coefficient C(E, x). Specifically, the second calculator 206c calculates the following Equation (2).

$$IDD'(x)=C(E,x)\times IDD(x) \quad (2)$$

where, IDD'(x) is an integral depth dose IDD after the correction, E is incidence the beam energy on the sensor unit 203, and x is a depth from the water surface. Since the difference from the water phantom is caused by a difference in nuclear cross sections of the material included in the sensor unit 203 and water and the like, the correction coefficient C(E, x) depends on the depth x from the water surface and the incidence energy E. The operator uses a Monte Carlo method or the like to calculate dose profiles of the radiation measuring device 101 and water, digitalizes a difference for each value of the incidence energy E and each depth x from the water surface, generates the correction coefficient C(E, x), and registers the correction coefficient C(E, x) in the main control device 206 in advance. The correction coefficient C(E, x) may be a function or a table.

In addition, even if the correction coefficient C(E, x) is generated on the basis of measurement data of the water phantom and measurement data of the radiation measuring device 101, the same effect can be obtained. In this case, the operator needs at first to temporarily register a correction coefficient C(E, x)=1 in the main control device 206 and uses the radiation measuring device 101 to measure a dose profile without the correction.

Lastly, the main control device 206 displays on a display (not shown) an IDD'(x) for each depth x from the water surface. The operator confirms and analyzes the dose profiles displayed on the display and evaluates results of adjusting the proton beam irradiation device 102 and the performance of the proton beam irradiation device 102.

A procedure for calculating the incidence energy E by the main control device 206 is described below.

First, the main control device 206 calculates a peak value from the obtained IDD(x) and normalizes the IDD(x) using the peak value as 100%. In addition, the main control device 206 causes the third calculator 206d to calculate a position at which a dose is 90% in a region deeper than a spot corresponding to the peak value, and the third calculator 206d treats the calculated position as a range R.

Next, the main control device 206 calculates the incidence energy E from a beforehand registered relational expression of the incidence energy E and the range R. The incidence energy E can be expressed by a function of the range R.

In the embodiment, a position at which a dose is 90% is treated as the range R. However, a position at which a dose is 80% may be defined as the range R, and a relational expression of the incidence energy E and the range R may be generated and registered in the main control device 206.

Next, the main control device 206 calculates the correction coefficient C(E, x) from the incidence energy E calculated according to the aforementioned procedure, corrects the IDD(x) according to Equation (2), and calculates the IDD'(x).

In the embodiment, the correction coefficient is expressed by C(E, x). The incidence energy E has a one-on-one relationship with the range R. Thus, even if the correction coefficient is expressed by C(R, x), the same effect can be obtained.

A profile shape of the IDD(x) is different from that of the IDD'(x). To appropriately calculate the range R from the IDD(x) before the correction, the following procedure may be added to the correction which will be performed by the main control device 206:

1) calculate the range R from the IDD(x);
2) correct the IDD(x) on the basis of the calculated range R;
3) calculate the range R from the IDD'(x); and
4) repeat processes 2) and 3) until the calculation result of the range R converges.

In the embodiment, the range R is calculated from the IDD(x), and the irradiation beam energy E is calculated from the relational expression of the irradiation beam energy E and the range R. However, the proton beam irradiation device 102 has information of the irradiation beam energy E. Thus, the proton beam irradiation device 102 may output the information of the beam energy E to the main control device 206, and the main control device 206 may calculate the correction coefficient C(E, x) on the basis of the information.

The correction coefficient to be used by the second calculator 206c of the main control device 206 is expressed by C(E, x) in the embodiment, but is not limited to this. If a radiation measuring device (e.g. having a configuration in which the electrodes of the charge collection printed boards 301 are each divided into parts arranged in a matrix form or into stripe parts, thus allowing ionized charges to be separately obtained from each of the divided electrodes) that is capable of measuring dose profiles in the depth direction and the lateral direction, the correction coefficient can be expressed by C(E, x, y, z), where y and z represent positions in the lateral direction. According to the invention, the same effect can be obtained with such a correction coefficient.

In addition, the radiation measuring device 101 according to the embodiment can measure a PDD in the volume irradiation with high precision. The volume irradiation is to form a uniform dose profile in an arbitrary region (referred to as an affected area or a target) of an object to be irradiated, in accordance with the procedure of the scanning irradiation method.

Figure 6:
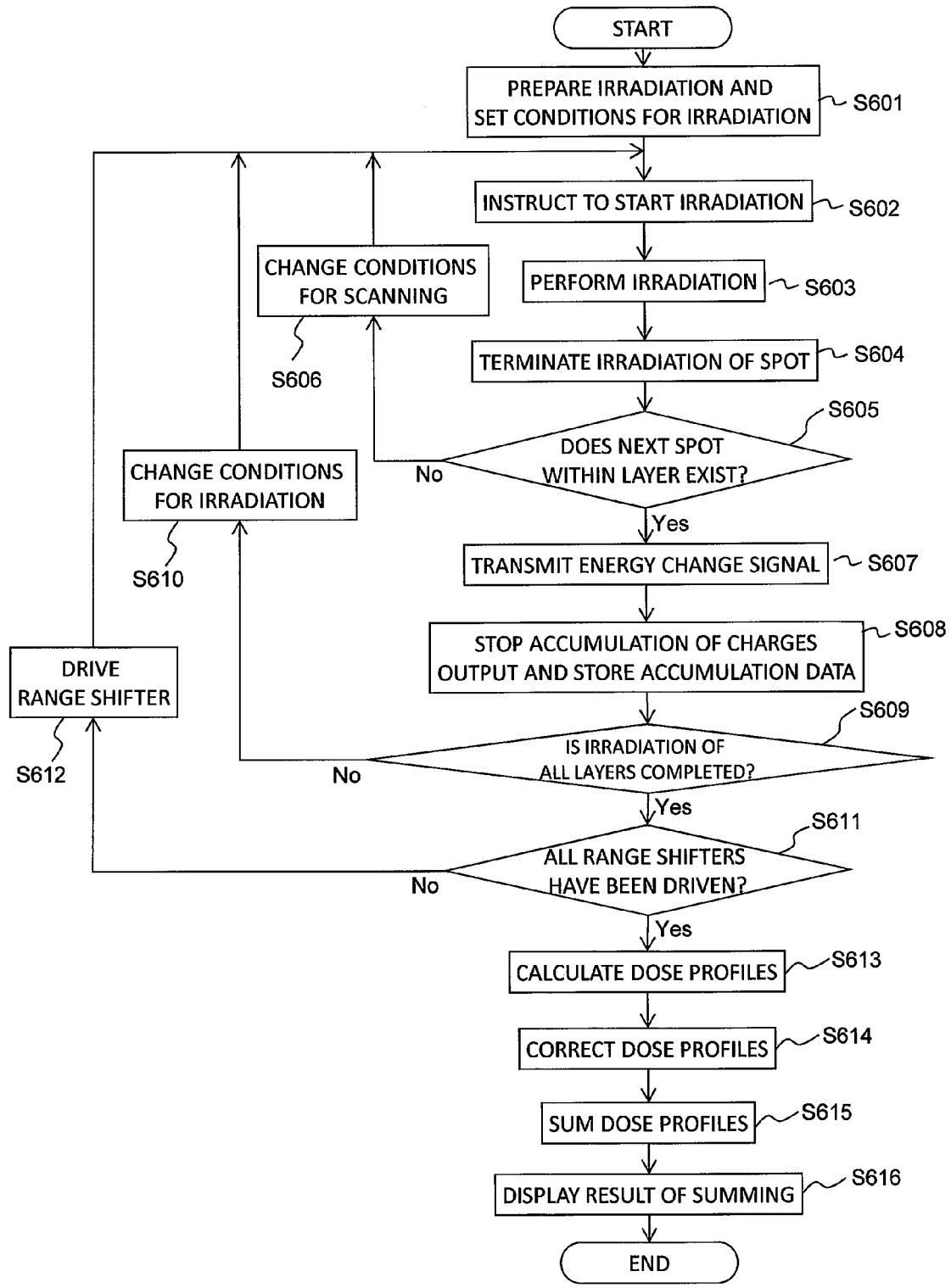
FIG. 6 is a flowchart of PDD measurement performed in volume irradiation and including operations of a proton beam irradiation device according to the embodiment of the invention and operations of the radiation measuring device according to the embodiment of the invention.

Operations of the proton beam irradiation device 102 and operations of the radiation measuring device 101 in PDD measurement performed in the volume irradiation are described with reference to FIG. 6. FIG. 6 is a flowchart of the PDD measurement performed in the volume irradiation, the flowchart including the operations of the proton beam irradiation device 102 and the radiation measuring device 101.

First, the radiation measuring device 101 is fixed onto the patient couch 114 in the irradiation chamber of the proton beam irradiation device 102 in the same manner as the IDD measurement.

Next, the patient couch 114 is moved so that the position of the radiation measuring device 101 is determined using, as the standard, the laser marker for determination of the position of a patient. In the embodiment, the position of the radiation measuring device 101 is determined so that the beam axis passes through the centers of the small electrodes 401 of the layers of the sensor unit 203.

After the position has been determined, the operator turns on the power supply of the range shifter driving control device 202, the high-voltage power supply 204, and the signal processing device 205, by use of the main control device 206. All the energy absorbers 201A of the range shifters 201 stand by while being placed out of the path of the beam.

Next, the operator sets desired measurement intervals in the main control device 206. In the embodiment, the operator sets the measurement intervals to 1.0 mm. In addition, the operator sets, from the main control device 206, conditions (the beam energy, the positions of spots to be irradiated, the number of the spots to be irradiated, and the like) of the volume irradiation to be performed by the proton beam irradiation device 102 (step S601). When the setting of the measurement intervals and the setting of the conditions are completed or the irradiation is completely prepared, the operator starts to instruct the irradiation with the beam (step S602).

The signal processing device 205 starts accumulating charges, and the radiation measuring device 101 is irradiated with the beam in accordance with the conditions set in the main control device 206 by the operator (step S603).

When the predetermined dose is added to a first spot (step S604), the proton beam irradiation device 102 stops the irradiation with the beam and determines whether a next spot exists (whether irradiation of all spots located at a certain depth (or in a certain layer) has been completed) (step S605). If the irradiation of all the spots located at the certain depth has yet to be completed, the proton beam irradiation device 102 scans the beam to the next spot (step S606). To scan the beam in the lateral direction, the scanning electromagnets included in the irradiation nozzle 110 are used.

If the proton beam irradiation device 102 determines that the predetermined dose has been applied to all the spots located at the certain depth (or in the certain layer) in step S605, the proton beam irradiation device 102 stops the irradiation with the beam and transmits an energy change signal to the signal processing device 205 (step S607).

Upon receiving the energy change signal, the signal processing device 205 stops accumulating charges, causes the accumulating unit 205a to digitalize accumulation values obtained from the small and large electrodes 401 and 402 of the layers of the sensor unit 203. Then the signal processing device 205 transmits the accumulation values to the main control device 206 through the output unit 205b. The main control device 206 stores the transmitted accumulation values in the storage unit 206a. After the completion of the storage, the signal processing device 205 resets all accumulation values stored therein (step S608).

After that, the proton beam irradiation device 102 determines whether the irradiation of all depths has been completed (whether the irradiation of all layers has been completed) (step S609). If the irradiation is not completed, the signal processing device 205 resets the accumulation values and restarts accumulating charges. The proton beam irradiation device 102 scans the beam in the depth direction, and the proton beam irradiation device 102 sets conditions for irradiation of spots located at a next depth with the beam (step S610), restarts the irradiation with the beam, and continues the processes of steps S602 to S610. The beam scanning in the depth direction is performed by changing the energy beam, which is caused by the range shifters mounted on the synchrotron 108, the irradiation nozzle 110, or the like.

In the next depth, as same manner as the previous depth, after predetermined dose has been applied to all spots located, the proton beam irradiation device 102 stops the irradiation with the beam and transmits the energy change signal to the signal processing device 205. Upon receiving the energy change signal, the signal processing device 205 stops accumulating charges, digitalizes accumulation values representing ionized charges and obtained from the small and large electrodes 401 and 402 of the layers of the sensor unit 203, and transmits the accumulation values to the main control device 206. The main control device 206 stores the transmitted accumulation values. After the completion of the storage, the signal processing device 205 resets all accumulation values stored therein. After resetting the accumulation values, the signal processing device 205 restarts accumulating charges. The proton beam irradiation device 102 scans the beam in the depth direction, and the proton beam irradiation device 102 restarts irradiating spots located at the next depth with the beam. Thus, the uniform doses are added to all the spots.

In this manner, the radiation measuring device 101 uses the energy change signal output from the proton beam irradiation device 102 to separately obtain accumulation values of ionized charges for each value of the beam energy and stores the accumulation values in the main control device 206.

If the proton beam irradiation device 102 determines that the irradiation of all the depths has been completed in step S609, the proton beam irradiation device 102 outputs the irradiation completion signal. Upon receiving the irradiation completion signal, the signal processing device 205 stops accumulating charges, digitalizes accumulation values representing ionized charges which were obtained from the small and large electrodes 401 and 402 of the layers of the sensor unit 203, and transmits the accumulation values to the main control device 206. The main control device 206 stores the transmitted accumulation values. After the completion of the storage, the signal processing device 205 rests all accumulation values stored therein.

Next, the proton beam irradiation device 102 determines whether all the range shifters have been driven in a scheduled manner (step S611). If the proton beam irradiation device 102 determines that not all the range shifters have not been driven, the main control device 206 instructs the range shifter driving control device 202 to insert an interested energy absorber 201A (step S612).

Specifically, in the embodiment, the energy absorbers 201A with the water equivalent thicknesses of 0.2 mm and 0.8 mm are first inserted. After the energy absorbers 201A has been inserted, the main control device 206 reinstructs the proton beam irradiation device 102 to perform the irradiation with the beam in accordance with the conditions initially set by the operator. The signal processing device 205 starts accumulating charges and the radiation measuring device 101 is irradiated with the beam. The measurement is repeated so that the total water equivalent thicknesses of the energy absorbers 201A inserted on the beam axis are 0.0 mm (all the energy absorbers 201A are placed out of the path of the beam), 1.0 mm, 2.0 mm, and 3.0 mm. Since the range shifters are operated in the aforementioned manner, the operator can use the radiation measuring device 101 having the sensors arranged at the intervals of 4.0 mm to measure PDDs of spots arranged at the intervals of 1.0 mm.

On the other hand, if the proton beam irradiation device 102 determines that all the range shifter have been driven, a process of calculating measurement results is performed.

If the inserted energy absorbers 201A has a total water equivalent thickness of r from the measurement result with the beam having a j-th energy value, the accumulating unit 205a of the signal processing device 205 calculates as Qs(i, j, r) the accumulated charges obtained from the small electrodes 401 facing the ionization layer i. When all measurements are completed in the same manner as the IDD measurement, the first calculator 206b of the main control device 206 converts Qs(i, j, r) into PDD(i, j, x) in accordance with the following Equation (3).

$$PDD(i,j,r) = N \times Qs(i,j,r) \quad (3)$$

The charge collection printed boards 301, the high-voltage application printed boards 302, and the water equivalent thicknesses of the ionization layers are measured and registered in the main control device 206 by the operator in advance. The main control device 206 converts PDD(i, j, r) into PDD(j, x) on the basis of the registered information (step S613). Note that x is a depth from the water surface.

The main control device 206 causes the third calculator 206*d* to calculate the range R from PDD(j, x) and calculate the energy E of the beam from the relational expression of the range R and the energy E of the beam in the same manner as the IDD measurement. In addition, the main control device 206 causes the second calculator 206*c* to calculate the correction coefficient C(E, x) on the basis of the calculated energy E of the beam and correct PDD(j, x) and obtain PDD' (j, x) (step S614). Specifically, the second calculator 206*c* calculates the following Equation (4).

$$PDD'(x) = C(E,x) \times PDD'(j,x) \quad (4)$$

In addition, the second calculator 206*c* of the main control device 206 sums PDD'(j, x) and obtains PDD"(x) in the volume irradiation according to the following Equation (5) (step S615).

$$PDD''(x) = EPDD'(j,x) \quad (5)$$

Lastly, the main control device 206 outputs a result of measuring PDD"(x) on a display 208 (step S616).

The operator confirms and analyzes the result and evaluates a result of adjusting the proton beam irradiation device 102 and the performance of the proton beam irradiation device 102.

The correction coefficient C(E, x) depends on the beam energy E. It is, therefore, difficult to correct measurement values obtained under a condition that beams with different energy values are used like the aforementioned volume irradiation.

According to the invention, however, the proton beam irradiation device 102 outputs the signal to the signal processing device 205 upon a change in the beam energy. The signal processing device 205 separately acquires measurement values at each reception of the signal. Thus, the dose measurement for each value of the energy in the volume irradiation is performed. Accordingly, in the volume irradiation in which beams with different energy values are used, it is possible to perform the correction using the correction coefficient C(E, x) and measure doses with high precision.

Figure 7:
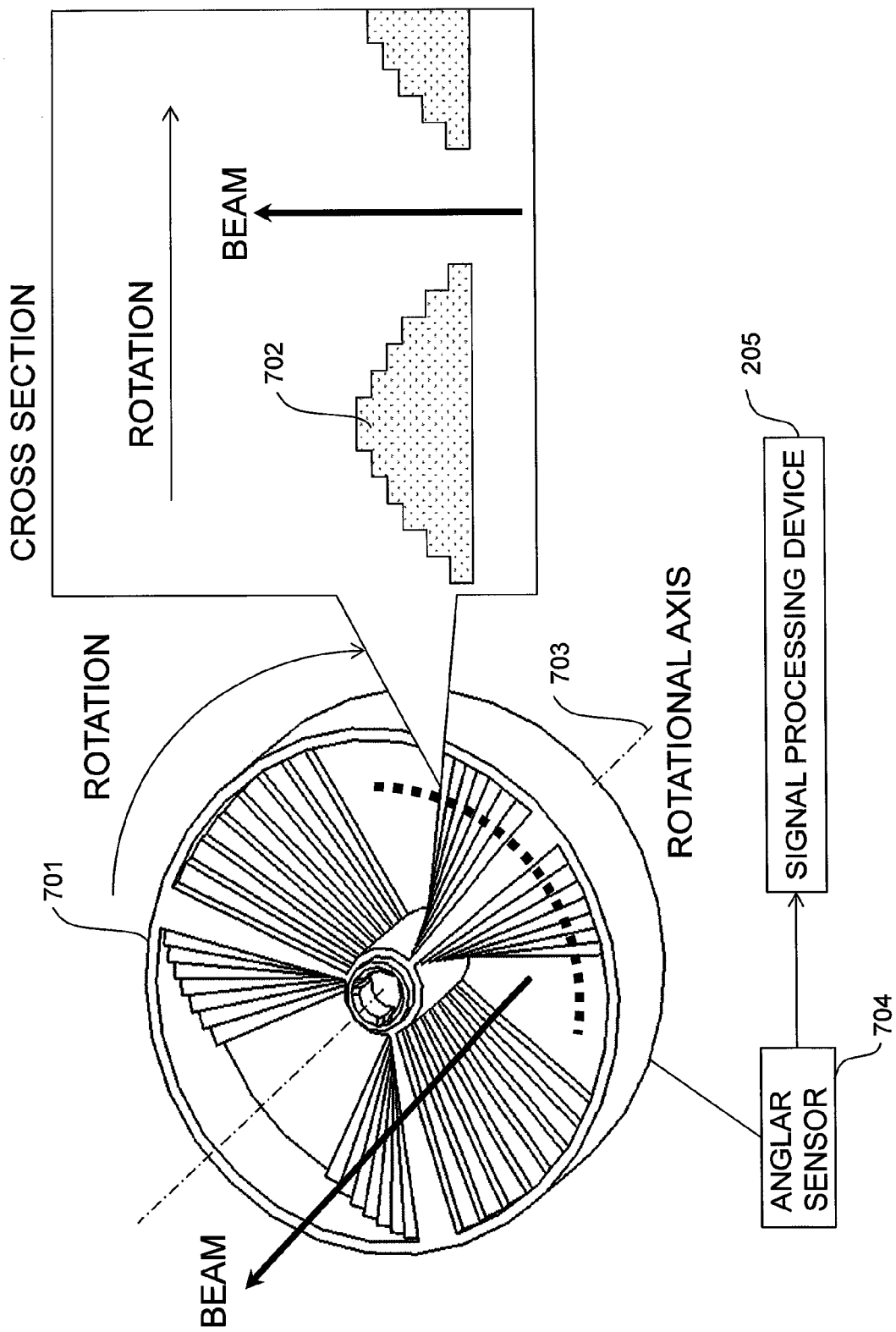
FIG. 7 is an outline diagram illustrating a range modulation wheel installed in an irradiation nozzle of the particle beam therapy device according to the embodiment of the invention.

The invention is also applicable to a proton beam irradiation device that has a range modulation wheel (RMW) in the irradiation nozzle 110. FIG. 7 is an outline diagram illustrating the range modulation wheel.

As illustrated in FIG. 7, the RMW 701 includes a plurality of blades having thicknesses that are different for rotational angles. When the RMW 701 rotates around a rotational axis 703, a beam passes through plates having different thicknesses at each specific rotational angle. Specifically, the beam energy is changed for each specific rotational angle. When beams propagate with different energy values for irradiation due to the rotation of the RMW 701, dose profiles that are uniform in the depth direction are formed. The RMW 701 is generally used for the scatterer irradiation method. If the RMW 701 and a scatterer formed of a tungsten plate or the like are used, dose profiles that are uniform in the lateral direction are also formed.

According to the invention, an angular sensor 704 is installed for the RMW 701. The operator registers, in the angular sensor 704, rotational angles (of, for example, 0 degrees, 10 degrees, 20 degrees, at which the thickness of a blade 702 changes. The angular sensor 704 detects a rotational angle of the RMW 701. When the thickness of the blade 702 changes, the angular sensor 704 transmits an energy change signal to the signal processing device 205. When receiving the energy change signal, the signal processing device 205 separately acquires measurement values. Specifically, the radiation measuring device 101 separately acquires data for each of the thicknesses of the blades 702 or for each energy value of the beam, thereby storing the data in the main control device 206. The radiation measuring device 101 can measure doses with high precision by correcting measurement values obtained according to the same procedure as the aforementioned scanning irradiation method.

According to the embodiment as described above, the radiation measuring device having the plurality of radiation sensors, typified by a multilayer ionization chamber, can measure doses with high precision and has a reduced difference from water phantoms. Thus, the multilayer ionization chamber can be used for a larger number of confirmation items, and a time for performance confirmation of therapy device is reduced.

The invention is not limited to the aforementioned embodiment and may be variously modified and changed and is applicable to the modifications and changes. The embodiment is described in detail in order to clarify the invention and is not necessarily limited to the devices having all the configurations described above.

For example, the proton beam irradiation device 102 may output a spot switching signal to the signal processing device 205 not when the energy change signal is transmitted and received, but when the irradiation with the beam is stopped after the predetermined dose has been applied to a certain spot. In this case, the signal processing device 205 may separately receive the measurement values according to the input signal.

Specifically, even if the method for separately acquiring a measurement value for each spot is used, the same effects as the invention can be obtained. This is due to the fact that the beam energy is constant within a single spot.

What is claimed is:
1. A radiation measuring device that detects a particle beam emitted by a particle beam irradiation device, comprising:
    a sensor unit having a plurality of sensor elements configured to generate charges in response to the particle beam;
    a signal processing device configured to separately collect, for each of the sensor elements, charges generated by each of the sensor elements of the sensor unit and perform an accumulation process; and
    a main control device configured to calculate a dose profile from accumulation values calculated in the accumulation process performed by the signal processing device,
    wherein the signal process device includes
        an accumulating unit configured to separately accumulate, for each of the sensor elements, charges output from each of the sensor elements for each timing of signal reception from the particle beam irradiation device, and
        an output unit configured to output the accumulation values calculated in the accumulation process performed by the accumulating unit to the main control device, and wherein the main control device includes
- a storage unit configured to store the accumulation values calculated for each timing of the signal reception from the signal processing device,
- a first calculator configured to calculate, from the accumulation values stored in the storage unit, the dose profile for each timing of the signal reception, and
- a second calculator configured to correct the dose profile for each timing of the signal reception calculated by the first calculator, and sum the corrected dose profiles.

2. The radiation measuring device according to claim 1, wherein the signal processing device receives the signal from the particle beam irradiation device when the irradiation energy of the particle beam is changed.

3. The radiation measuring device according to claim 1, wherein the signal processing device receives the signal from the particle beam irradiation device when an irradiation spot for the particle beam is changed.

4. The radiation measuring device according to claim 1, wherein the second calculator of the main control device corrects the dose profile using a coefficient that depends on the irradiation energy of the particle beam.

5. The radiation measuring device according to claim 1, wherein the sensor unit has a structure in which the sensor elements are stacked in a propagation direction of the particle beam, and
wherein the main control device further includes a third calculator configured to calculate a range of the particle beam from the dose profiles calculated by the first calculator, each the dose profiles being obtainable for each timing of the signal reception.

6. A particle beam therapy device comprising:
the particle irradiation device; and
the irradiation measuring device according to any of claims 1 to 5.

7. The particle beam therapy device according to claim 6, wherein the particle beam irradiation device includes a range modulation wheel, and
wherein the particle beam irradiation device outputs a signal to the signal processing device of the radiation measuring device when a thickness of the range modulation wheel is changed.

8. The particle beam therapy device according to claim 6, wherein the particle beam irradiation device outputs a value of the beam energy to the main control device.

9. A method for calculating a dose profile of a particle beam emitted by a particle beam irradiation device, comprising the steps of:
- arranging a sensor unit having a plurality of sensor elements configured to generate charges in response to the particle beam in a propagation direction of the particle beam;
- irradiating the sensor unit with the particle beam, separately collecting, for each of the sensor elements, charges generated by each of the sensor elements of the sensor unit, and separately accumulating, for each of the sensor elements, charges output from each of the sensor elements for each timing of a signal reception from the particle beam irradiation device, thereby calculating accumulation values;
- calculating, from the accumulation values calculated in the accumulated value calculation step, dose profile for each timing of the signal reception from the particle irradiation device;
- correcting the dose profiles calculated in the dose profile calculation step, each of the dose profiles being obtainable for each timing of the signal reception; and
- summing the dose profiles corrected in the correction step.

10. The dose profile calculation method according to claim 9, wherein in the correction step, the dose profiles are corrected using a coefficient that depends on the irradiation energy of the particle beam.

* * * * *